United States Patent [19]

Couvertier, II

[11] Patent Number: 5,092,853
[45] Date of Patent: Mar. 3, 1992

[54] AUTOMATIC RETRACTABLE MEDICAL NEEDLE AND METHOD

[76] Inventor: Douglas Couvertier, II, 17410 SW. 59th Ct., Fort Lauderdale, Fla. 33331

[21] Appl. No.: 650,419

[22] Filed: Feb. 4, 1991

[51] Int. Cl.⁵ .............................................. A61M 5/32
[52] U.S. Cl. ..................................... 604/195; 604/110
[58] Field of Search ............... 604/110, 195, 240, 241, 604/243, 218, 228, 198, 263

[56] References Cited

U.S. PATENT DOCUMENTS

| | | | |
|---|---|---|---|
| 1,526,824 | 2/1925 | Bock | 604/241 |
| 2,855,927 | 10/1958 | Henderson | 604/243 |
| 3,108,592 | 10/1963 | Hassing et al. | 604/243 |
| 4,235,232 | 11/1980 | Spaven et al. | 604/243 |
| 4,735,618 | 4/1988 | Hagen | 604/192 |
| 4,747,835 | 5/1988 | Sandhaus | 604/192 |
| 4,826,489 | 5/1989 | Haber et al. | 604/195 |
| 4,832,696 | 5/1989 | Luther | 604/164 |
| 4,842,586 | 6/1989 | Hogan | 604/192 |
| 4,909,794 | 3/1990 | Haber et al. | 604/195 |
| 4,911,693 | 3/1990 | Paris | 604/192 |
| 4,928,824 | 5/1990 | Barasch | 206/365 |
| 4,935,012 | 6/1990 | Magre et al. | 604/192 |
| 4,950,241 | 8/1990 | Ranford | 604/195 |
| 4,994,034 | 2/1991 | Botich et al. | 604/198 |

Primary Examiner—John D. Yasko
Assistant Examiner—Sharon Finkel
Attorney, Agent, or Firm—Oltman and Flynn

[57] ABSTRACT

A guard mechanism for a medical needle has a hub and a hollow needle portion. The guard includes a tubular sheath, a spring within the sheath which biases the hub to draw the needle into the sheath. Jaws project from an end of the sheath for gripping the needle portion to prevent the spring from drawing the needle portion into the sheath. A body surrounds the sheath for grasping and holding the guard mechanism, and has a port through which the jaws project, the jaws being resiliently biased to bear against the port, such that when the sheath is moved toward the port, the jaws slide out from the port and are thereby freed to resiliently expand, thereby releasing the needle portion and permitting the spring to withdraw the needle portion into the sheath.

10 Claims, 4 Drawing Sheets

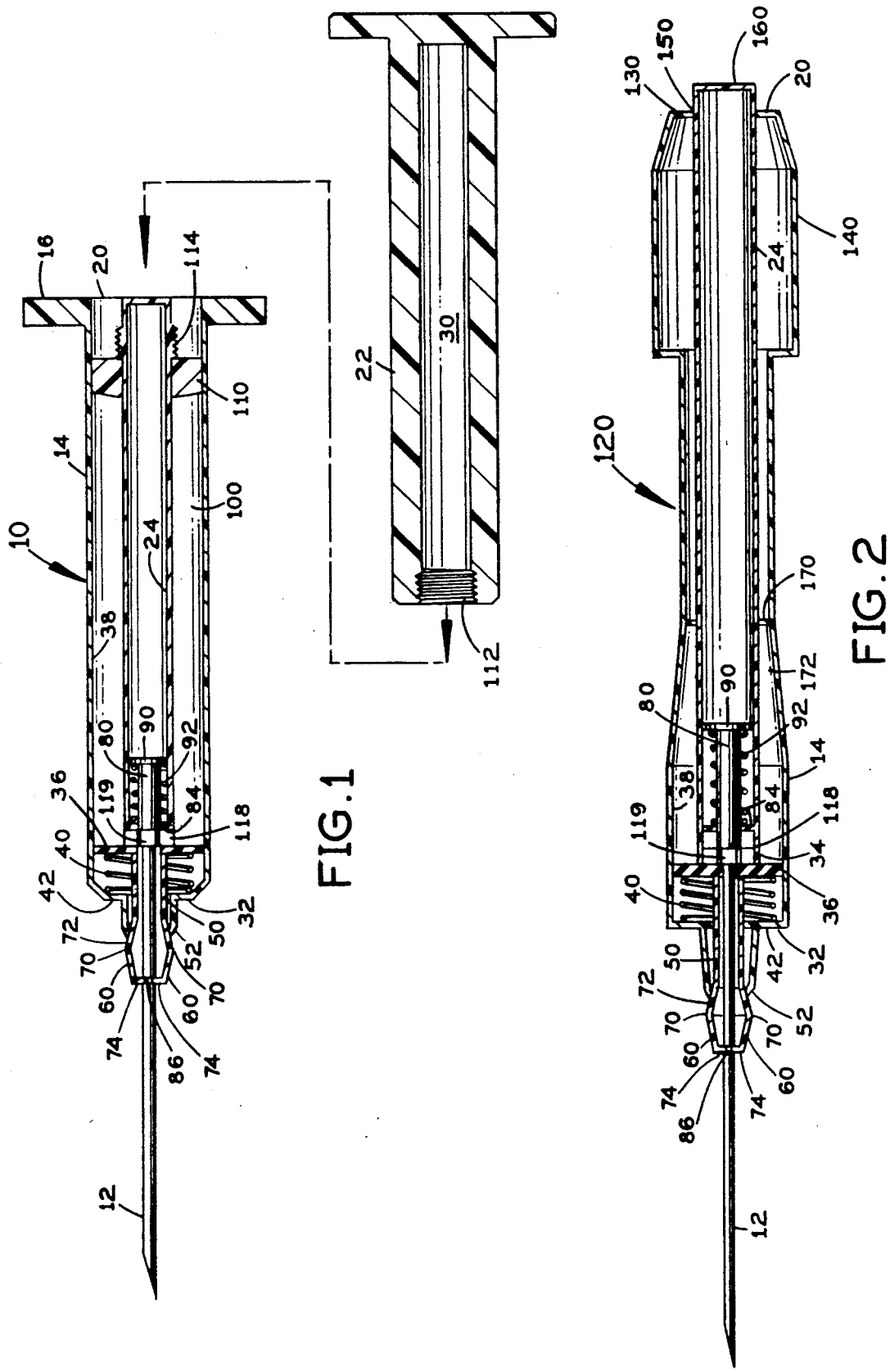

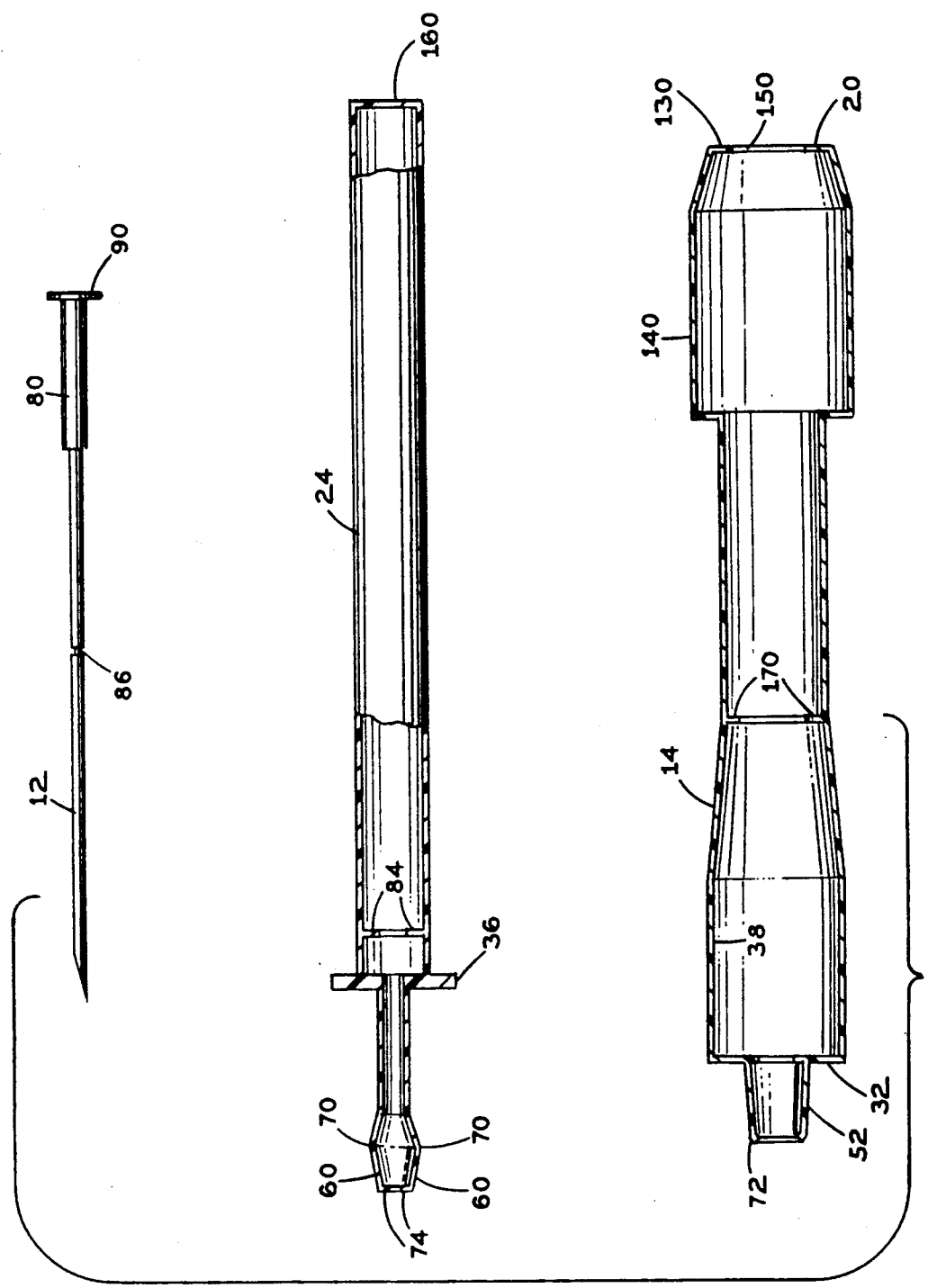

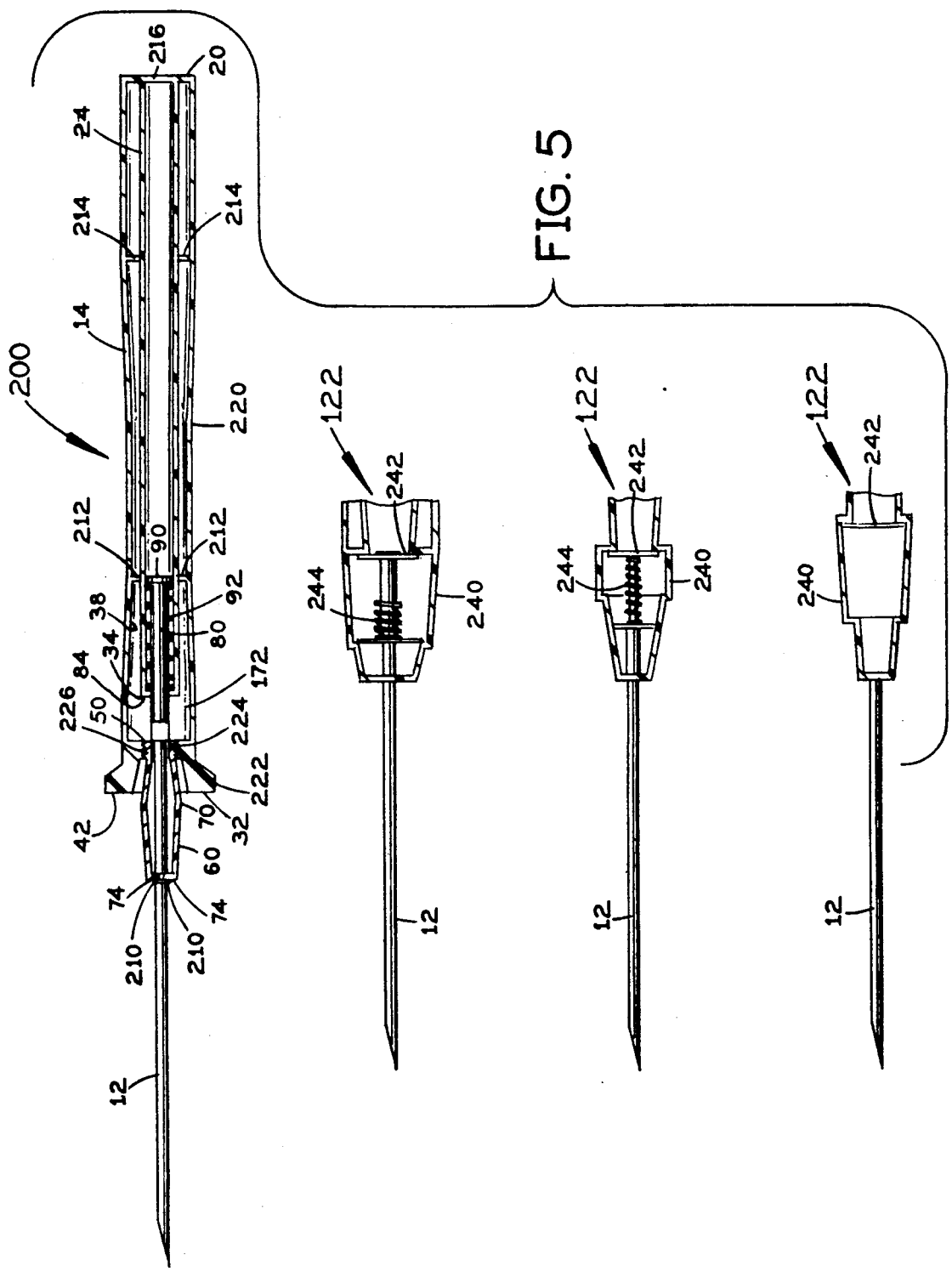

AUTOMATIC RETRACTABLE MEDICAL NEEDLE AND METHOD

BACKGROUND OF THE INVENTION

1. Field of the invention

The present invention relates generally to the field of protective guards for medical needles, and more specifically to a spring-loaded needle which quickly and semi-automatically retracts into a protective guard assembly upon completion of use.

2. Description of the Prior Art:

The advent of Acquired Immune Deficiency Syndrome (AIDS) has drawn attention to and substantially increased the dangers of being stuck by medical needles. It is recognized that even a minute transfer of body fluid from a person infected with a disease such as AIDS into another person's bloodstream can transmit the disease. The danger is not confined to the medical community. Increasing quantities of illegally dumped medical waste, including countless used hypodermic needles, have recently washed up on public beaches. Recognition of these dangers has lead to the development of a variety of devices for permanently shielding the tips of used medical needles.

One such device is disclosed in Magre et. al., U.S. Pat. No. 4,935,012, issued on June 19, 1990. Magre teaches a protective sheath which slides to three positions on an extended needle support hub. The sheath has a close-fitting needle exit port at the remote end of the sheath extending through an interior, conical protrusion. The initial sheath position encloses the needle point within the exit port and thus shields it against accidental contact. The second position exposes the needle for use. The third position encloses the needle point within the sheath itself and misaligns the point from the exit port to prevent further point exposure. A problem with Magre is that the handler must somehow grasp the sheath to pull it over the needle point after use. Doing this with ones hands creates a danger of needle injury. Otherwise a tool is required. In the mean time, the needle point is exposed and dangerous. Another problem is that misaligning the point from the exit port does not completely assure that it will not re-emerge.

A protective sheath device separate from the needle structure is recited in Barasch, U.S. Pat. No. 4,928,824, issued on May 29, 1990. The sheath itself is simply a tube for enclosing the needle. The needle hub snugly fits into the sheath entry port after the needle is inserted in the sheath. One embodiment shows a radial guard surrounding the sheath for shielding the handler from the point during needle insertion. Another embodiment provides a wide, coaxial outer tube for positioning the handler's fingers away from the sheath entry port. Once again, despite the radial guard or outer tube, the handler must grasp the sheath device while inserting the exposed point. If done enough times, and particularly under rushed and stressful conditions, a significant risk of accidental needle injury is presented. And, in the interval between use and insertion into the sheath, the needle point remains dangerously exposed.

Paris, U.S. Pat. No. 4,911,693, issued on Mar. 27, 1990, is essentially a variation of Magre. A telescoping spring-loaded sleeve for enclosing a needle has three positions. The first releasably locks the sleeve to enclose the point. The second leaves the point enclosed but permits sleeve telescoping against spring resistance. This position permits the needle to enter the patient while the sleeve presses against the surrounding skin. The third position again encloses the needle point, but tabs between inner and outer sleeve sections permanently lock the sleeve to prevent further telescoping and point exposure. A problem is that the handler must grasp the sleeve section nearest the point to lock it. Simply bumping the end of the sleeve prior to locking can cause the point to protrude and injure.

A tool for withdrawing a needle from a patient directly into a sheath is provided in Hogan, U.S. Pat. No. 4,842,586, issued on June 27, 1989. This tool has a cradle, a cradle stem and a tubular sheath which slides over the cradle and stem. The cradle receives the hub. Then the sheath is held against the skin while the stem is pulled outward. This action draws the needle into the sheath. Spring-loaded tabs lock the stem in the withdrawn position. The invention is intended primarily for withdrawing spinal needles, although is described as applicable to other needle types. A problem with Hogan is that the syringe or IV tube attached to the needle must be removed independently of the needle. This is particularly unpleasant for the patient receiving a hypodermic injection, because the needle must remain embedded while the syringe is removed and the tool positioned to engage the needle hub. In addition, contaminated body fluids can escape through the embedded needle during this procedure. This fluid could make contact with an open sore or cut on the needle handler, thus transmitting disease.

Luther, U.S. Pat. No. 4,832,696, issued on May 23, 1989, discloses a locking needle guard similar to that of Magre. A telescoping sleeve is retracted the hub of a needle. A cap, which initially covers and encloses the needle, is removed to expose the needle for use. When the injection is completed, the sleeve is held against the skin of the patient while the needle is withdrawn, so that the needle remains enclosed. When the sleeve is fully extended, it locks to prevent further telescoping and needle exposure. A catheter may be inserted in this manner by placing it over the needle so that the exposed needle point permits insertion. A problem with this arrangement is that the handler must grasp the sleeve near the needle point during withdrawal to keep the needle covered. This close proximity to the point of the used needle is inherently dangerous.

A variation of Barasch is disclosed in Sandhaus, U.S. Pat. No. 4,747, 835, issued on May 31, 1988. A sheath device for a used needle is provided having a radial guard surrounding its entry port to shield the handler from the point. A problem, once again, is that the handler must grip the sheath device while inserting the point, thus creating the potential for accidental sticking.

Finally, there is Hagen, U.S. Pat. No. 4,735,618, issued on Apr. 5, 1988. Hagen is a variation of Magre. A collapsible sheath has a narrow needle exit port. The sheath is collapsed to drive the needle through the port and expose it for use. Then the sheath is re-extended to withdraw the needle point through the port and inside the sheath. The sheath is then bent to misalign the exit port so that the needle is not re-exposed. The problems presented by the Hagen design are the same as those of Magre. One must grasp the sheath near the used needle point to re-extend it to cover the needle. During the interval between use and sheath re-extension, the dangerous, used needle point is exposed. And, again, misaligning does not completely assure that the point will not re-emerge.

It is thus an object of the present invention to provide a medical needle guard which does not require the handler to touch the guard near an exposed, used needle.

It is another object of the present invention to provide a medical needle guard which reliably locks the needle away from contact after use.

It is still another object of the present invention to provide a needle guard which is simple in design and easy to use.

It is finally an object of the present invention to provide a needle guard which withdraws the needle automatically when use is completed.

SUMMARY OF THE INVENTION

The present invention accomplishes the above-stated objectives, as well as others, as may be determined by a fair reading and interpretation of the entire specification.

A guard mechanism is provided for a medical needle having a hub and a hollow needle portion. The guard includes a tubular sheath, a spring within the sheath which biases the hub to draw the needle into the sheath. Jaws project from an end of the sheath for gripping the needle portion to prevent the spring from drawing the needle portion into the sheath. A body surrounds the sheath for grasping and holding the guard mechanism, and has a port through which the jaws project, the jaws being resiliently biased to bear against the port, such that when the sheath is moved toward the port, the jaws slide out from the port and are thereby freed to resiliently expand, thereby releasing the needle portion and permitting the spring to withdraw the needle portion into the sheath.

The body can be a hypodermic syringe, having a plunger entry end and a needle end, which holds fluid to be injected between the sheath and the body. The jaws are attached to the sheath and the spring biases the sheath toward the plunger entry end of the body to hold the jaws within the port and the body means. The syringe plunger has an axial bore which slides over the sheath.

A method for retracting a hypodermic needle into a syringe with such a guard mechanism includes the steps of: placing fluid to be injected inside the syringe, placing the plunger in the plunger end of the syringe, depressing the plunger until the fluid is discharged through the needle, depressing the plunger until the guard mechanism retracts the needle into the sheath.

BRIEF DESCRIPTION OF THE DRAWINGS

Various other objects, advantages, and features of the invention will become apparent to those skilled in the art from the following discussion taken in conjunction with the following drawings, in which:

FIG. 1 is a cut-away, plan view of the hypodermic syringe embodiment, showing the plunger separately.

FIG. 2 is a cut-away, plan view of the intravenous embodiment.

FIG. 3 is a cut-away, plan view of the major elements forming the intravenous embodiment, showing, from top to bottom, the needle, the sheath, and the body of the device.

FIG. 5 is another cut-away, plan view of the catheter insertion embodiment, showing at the top the complete device, and below, three catheter and hub designs. The uppermost catheter design features an interior coil spring, the middle catheter design features an interior coil spring, and the bottom catheter design features leaf springs.

DETAILED DESCRIPTION OF THE PREFERRED EMBODIMENTS

Figure 4:
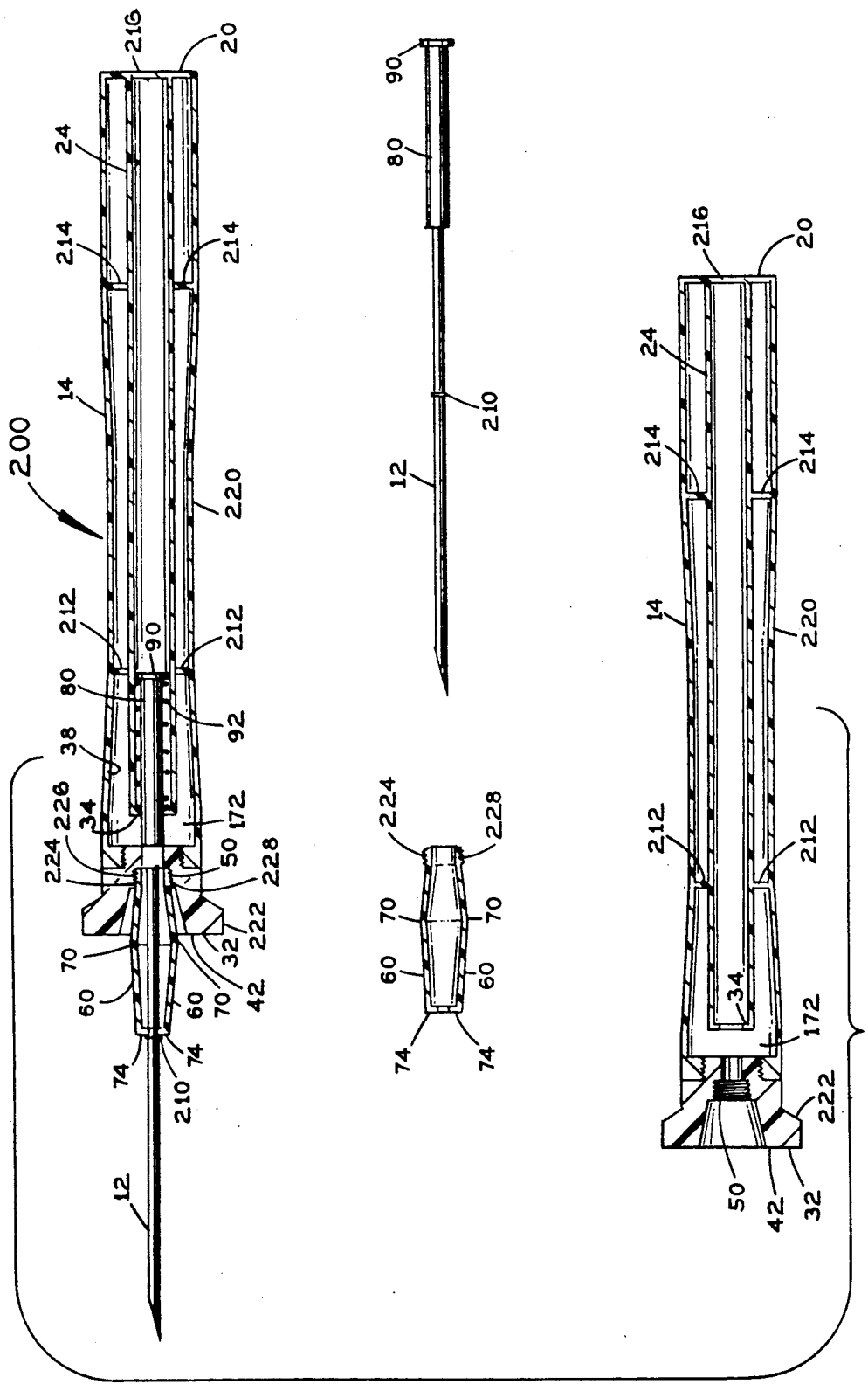
FIG. 4 is cut-away, plan view of the catheter insertion embodiment, showing, from top to bottom, the complete device, the needle, the jaws, and the unitary body and sheath.

As required, detailed embodiments of the present invention are disclosed herein; however, it is to be understood that the disclosed embodiments are merely exemplary of the invention which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Reference is now made to the drawings, wherein like characteristics and features of the present invention shown in the various FIGURES are designated by the same reference numerals.

First Preferred Embodiment

Referring to FIG. 1, a hypodermic syringe 10 with a semiautomatically retracting needle 12 is disclosed. Syringe 10 is formed of a tubular body 14 with finger grip wings 16 at its control end 20 and a plunger 22 which snugly fits inside body 14. Mounted co-axially within body 14 is a tubular sheath 24 for needle 12. Plunger 22 has an axial bore 30 which receives sheath 24 when plunger 22 is inserted into control end 20 of body 14.

Near the needle end 32 of body 14, sheath 24 ends. The needle end 34 of sheath 24 has fingers 118 which extend into contact with a rubber seal 36. A coil spring 40 extends between seal 36 and the end wall 42 of body 14. Wall 42 has a centrally located exit port 50 with an axial cylindrical ridge 52. Two jaws 60 project from seal 36 and extend through port 50 and ridge 52. Jaws 60 are formed of a resilient material and are biased to take an open position. They are pressed together by contact with ridge 52.

An outwardly directed bulge 70 is formed in each jaw 60 adjacent to the remote edge 72 of ridge 52. Spring 40 presses sheath 24, seal 36 and jaws 60 toward control end 20 of body 14, and thus presses bulges 70 against edge 72. Edge 72 is beveled inside to direct the pressure against bulges 70 to close jaws 60. Each jaw 60 has at least one tooth 74 directed toward opposing jaw 60. The hub 80 of needle 12 is contained within the needle end 34 of sheath 24. A flange 84 attached to the interior of sheath 24 surrounds and positions hub 80. Needle 12 extends through end 34, port 50 and out between jaws 60. At least one circumferential groove 86 in the exterior of needle 12 receives teeth 74. This groove and tooth interlock prevents needle 12 from moving while jaws 60 are closed.

A flange 90 is formed at the base of hub 80. A second coil spring 92 is provided inside sheath 24, surrounding hub 80 and extending between flange 90 and flange 84. Spring 92 to bias needle 12 toward withdrawal into sheath 24.

The fluid to be injected fills the annular area 100 between sheath 24 and body 14. Seal 36 retains fluid at needle end 32 of syringe 10 while an annular rubber stopper 110 retains fluid at the control end 20. Threads 112 in the end of axial bore 30 screw onto a threaded flange 114 on stopper 110. A portion of hub 80 extends through end 34 of outside sheath 14 and its circumference is cut to form an array of axially-directed fingers 119. Fingers 119 are connected to needle 12.

Method

In practicing the invention, the following method may be used. Fluid is poured into area 100 and stopper 110 is inserted in control end 20. Plunger 22 is placed inside body 14 and screwed to stopper 110. Needle 12 is inserted into the patient. Then plunger 22 is pressed into body 14, pressing stopper 110 against the fluid. Fluid passes between fingers 118 into needle 12 and exits into the patient. The escape of fluid between fingers 118 and 119 prevents fluid pressure from increasing sufficiently to compress spring 40.

Once the fluid is all expelled, syringe 10 is pulled away from the patient, thereby withdrawing needle 12. Once needle 12 is withdrawn from the patient, plunger 22 is further pressed and until it bears against and depresses seal 36. As seal 36 moves, so do sheath 24 and jaws 60. As jaws 60 slide out of ridge 52, their resiliency causes them to expand. The expansion of jaws 60 draws teeth 74 out of groove 86. This frees needle 12 and spring 92 quickly retracts needle 12 into sheath 24. There is no way to grip needle 12 and overcome the force of spring 92 to pull needle 12 back out of sheath 24. Thus, syringe 10 can be safely discarded.

The automatic retraction of needle 12 upon completion of the injection eliminates any chance of the user touching the used needle 12. It assures that no significant time elapses between injection and retraction and prevents the used needle 12 from being dangerously exposed.

Second Preferred Embodiment

A device 120 for an intravenous catheter 122 insertion has the same needle 12 retraction mechanism provided in the first embodiment. See FIGS. 2 and 3. An IV tube attaches to catheter 122. The body 14 of device 120 differs in several ways from that of the first embodiment. The device does not contain fluid to be injected. An end wall 130 is provided at control end 20 of body 14.

Body 14 is transparent and contoured for easy grasping. It tapers from needle end 32 across about two-thirds of the distance to control end 20. Then body 14 expands to form a bulbous portion 140. Sheath 24 projects out of a close-fitting port 150 in control end 20. A flange 170 extends from the inner wall of body 14 and closely surrounds and guides sheath 24.

Catheter 122 is of such a length that the point of needle 12 protrudes from catheter 122, permitting insertion into the patient. A flash chamber 172 indicates when a vein has been pierced. Flash chamber 172 comprises the area between flange 170 and seal 36, and between body 14 and sheath 24. A visible burst of blood passes through needle 12 and fingers 118 into chamber 172 when a vein is pierced. Once a vein is thus located and catheter 122 inserted, device 120 is pulled away from the patient, thereby withdrawing needle 12 from catheter 122 and from the patient.

Then needle 12 is retracted by simply depressing projecting portion 160 of sheath 24. This pushes seal 36 against spring 40 and moves bulges 70 of jaws 60 out of ridge 52. This permits jaws 60 to open and release groove 86 in needle 12. Upon release, spring 92 rapidly retracts needle 12 into sheath 24. The ability to operate the retraction mechanism from control end 20 eliminates the need to touch the device near the needle 12 end.

Third Preferred Embodiment

Finally, a catheter 122 insertion device 200 has essentially the same needle 12 retraction mechanism provided in the first and second embodiments. A flash chamber 172 is provided as in the previous embodiment. A lip 210 is provided around needle 12 to engage teeth 74 of jaws 60, although a groove may alternatively serve this purpose. See FIG. 4. Sheath 24 is fixed within body 14 by two connecting flanges 212 and 214. Control end 20 is closed by a solid end wall 216. Body 14 is contoured for easy handling, such that it tapers at its middle section 220. A radial guard 222 surrounds needle end 32. No seal 36 or spring 40 is provided because sheath 24 does not move relative to body 14. Jaws 60 are attached to an annular base 228 having threads 224. Base 228 is screwed into threads 226 inside exit port 50. Device 200 is provided with a catheter 122 already fitted over jaws 60 which holds jaws 60 together until catheter 122 is inserted. Catheter 122 is of such a length that the point of needle 12 protrudes from catheter 122.

Needle 12 and catheter 122 are inserted into the patient. The point of needle 12 penetrates the tissue so that catheter 122 can enter. The user presses at least one of their fingers against the skin over the embedded catheter 122 and pulls device 200 out of catheter 122. Jaws 60 are thus freed to move and spread release needle 12, which in turn retracts into sheath 24. The user continues to press their fingers against the skin to prevent the flow of blood out of catheter 122 until the IV tube can be attached.

Catheter 122 has a hub 240 which fits over jaws 60 and includes within its interior a washer 242 mounted on a spring 244. See FIG. 5. It is hub 240 of catheter 122 which holds jaws 60 together. Spring 244 may be a coil spring which needle 12 slides axially through or two converging leaf springs which needle 12 slides between. When the needle 12 is removed, the leaf springs overlap each other and seal completely. FIG. 5 illustrates these alternatives. Needle 12 extends through washer 242 and spring 244, which seal catheter 122. Jaws 60 press against washer 242, during catheter 122 insertion.

While the invention has been described, disclosed, illustrated and shown in various terms or certain embodiments or modifications which it has assumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

I claim as my invention:

1. A hypodermic syringe and needle for injecting fluid having a first position with the needle extended for use and a second position with the needle safely retracted, comprising:

a tubular body for containing the fluid to be injected having an interior surface and a first end and a second end, and having a wall across the first end and a hole in the wall having an edge, a tubular sheath positioned within said tubular body having a second end at the second end of the tubular body and a first end within the tubular body, the first end of the tubular sheath having an interior flange and the second end being closed by an integral cap, the longitudinal axis of the tubular sheath being aligned with the center of the hole and parallel with the longitudinal axis of the tubular body, the needle having a conduit portion and a tubular base portion at one end of the conduit portion, the tubular base portion having a circumferential wall with at least one perforation and a sealed end cap opposite the conduit portion, the tubular base portion extending into the tubular sheath and having an exterior flange at the sealed end which makes sliding contact with the interior surface of the tubular sheath, the conduit portion extending through the hole in the wall, first spring means extending between the flange of the tubular base portion or the needle and the flange of the tubular sheath biasing said flanges away from each other, an annular seal which surrounds and makes sealing contact with the conduit portion of the needle and extends to and makes sealing contact with the interior surface of the tubular body, a pair of jaws extending perpendicularly from the annular seal through the hole in the wall, the jaws being resiliently biased to open and the portion of each jaw extending outside the tubular body having an outwardly bowed exterior surface, the bowed exterior surfaces together being wider than the hole when the jaws are closed, second spring means between the seal and the wall which bias the seal away from the wall, and thus pull the bowed exterior surfaces of the jaws against the edge of the hole, said second spring means having biasing of sufficient magnitude to overcome the biasing of the jaws and to pull the bowed portions of the jaws into the hole to an extent which closes the jaws, the jaws closing around and gripping the needle to hold the needle in the first position, an annular plunger which enters the second end of the tubular body and sealingly fits between the tubular sheath and the tubular body, such that depressing the plunger drives the fluid out of the tubular body through the at least one perforation in the tubular base portion of the needle and through the conduit portion of the needle and then makes contact with and presses against the seal, depressing the annular seal and thereby pushing the bowed exterior surfaces of the jaws out of the hole, permitting the jaws to resiliently open, thereby releasing the needle which slides into the tubular sheath to take the second position.

2. A hypodermic syringe and needle as in claim 1, additionally comprising:

a jaw securing tube surrounding the hole in the wall and coaxial with the tubular sheath, and extending outside the tubular body.

3. A hypodermic syringe and needle as in claim 1, wherein the plunger has a detachable annular seal which surrounds the tubular sheath and makes sealing contact with the tubular sheath and the interior surface of the tubular body.

4. An apparatus for inserting an intravenous catheter, wherein the apparatus has a first position for insertion and a second position for apparatus withdrawal from the catheter, comprising:

a tubular body for the user to hold having an interior surface and a first end and a second end, and having a wall across the first end and a hole in the wall having an edge, a tubular sheath positioned within said tubular body having a second end protruding from the second end of the tubular body and a first end within the tubular body, the first end of the tubular sheath having an interior flange and the second end being closed by an integral cap, the longitudinal axis of the tubular sheath being aligned with the center of the hole and parallel with the longitudinal axis of the tubular body, a needle over which the intravenous catheter is fitted, said needle having a conduit portion with a point at one end and a tubular base portion at the other end, the tubular base portion having a sealed end cap opposite the conduit portion, the tubular base portion extending into the tubular sheath and having an exterior flange at the sealed end which makes sliding contact with the interior surface of the tubular sheath, the conduit portion extending through the hole in the wall, first spring means extending between the flange of the tubular base portion of the needle and the flange of the tubular sheath biasing said flanges away from each other, an annular seal which surrounds and makes sealing contact with the conduit portion of the needle and extends to and makes sealing contact with the interior surface of the tubular body and which is attached to the first end of the tubular sheath, a pair of jaws extending perpendicularly from the annular seal through the hole in the wall, the jaws being resiliently biased to open and the portion of each jaw extending outside the tubular body having an outwardly bowed exterior surface, the bowed exterior surfaces together being wider than the hole when the jaws are closed, second spring means between the seal and the wall which bias the seal away from the wall, and thus pull the bowed exterior surfaces of the jaws against the edge of the hole, said second spring means having biasing of sufficient magnitude to overcome the biasing of the jaws and to pull the bowed portions of the jaws into the hole to an extent which closes the jaws, the jaws closing around and gripping the needle to hold the needle in the first position, such that depressing the exposed second end of the tubular sheath depresses the annular seal, thereby pushing the bowed exterior surfaces of the jaws out of the hole, permitting the jaws to resiliently open, thereby releasing the needle which slides into the tubular sheath to take the second position.

5. An apparatus for inserting an intravenous catheter as in claim 4, additionally comprising:

a jaw securing tube surrounding the hole in the wall and coaxial with the tubular sheath, and extending outside the tubular body.

6. An apparatus for inserting an intravenous catheter as in claim 4, wherein the tubular body has a contoured shape to permit the user to hold the apparatus more securely.

7. An apparatus for inserting an intravenous catheter, wherein the apparatus has a first position for insertion and a second position for apparatus withdrawal from the catheter, comprising:
- a tubular body for the use to hold having an interior surface and a first end and a second end, and having a wall across the first end and a hole in the wall having an edge,
- a tubular sheath positioned within said tubular body by rib members, having a second end at the second end of the tubular body and a first end within the tubular body, the first end of the tubular sheath having an interior flange and the second end being closed by an integral cap, the longitudinal axis of the tubular sheath being aligned with the center of the hole and parallel with the longitudinal axis of the tubular body,
- a needle over which the intravenous catheter is fitted, said needle having a conduit portion and a tubular base portion at one end of the conduit portion, the tubular base portion having a sealed end cap opposite the conduit portion, the tubular base portion extending into the tubular sheath and having an exterior flange at the sealed end which makes sliding contact with the interior surface of the tubular sheath, the conduit portion extending through the hole in the wall,
- spring means extending between the flange of the tubular base portion of the needle and the flange of the tubular sheath biasing said flanges away from each other,
- a pair of jaws extending perpendicularly from the edge of the hole outside the tubular body, the jaws being resiliently biased to open an the portion of each jaw extending outside the tubular body having an outwardly bowed exterior surface and the needle having a hub portion which surrounds the jaws and holds them together, such that removal of the intravenous catheter frees the jaws to resiliently open, thereby releasing the needle which slides into the tubular sheath to take the second position.

8. An apparatus for inserting an intravenous catheter as in claim 4, wherein the intravenous catheter comprises tubular catheter stem means and hub means which surround the conduit portion of the needle and press against the jaws when the intravenous catheter is fitted onto the apparatus.

9. A hypodermic syringe and needle as in claim 1, wherein the tubular body is transparent and the syringe includes flash chamber means formed between the tubular body and the tubular sheath, and the needle portion is in fluid communication with the flash chamber means through the base portion, the purpose of the flash chamber means being to receive blood visibly to the user to indicate that a vein has been pierced.

10. A method for inserting an intravenous catheter into a patient with an apparatus as in claim 4, comprising the steps of:
- placing the catheter over the needle so that the catheter hub fits over the jaws and the tip of the needle projects out from the catheter,
- inserting the needle and catheter into the patient,
- withdrawing the needle from the patient, leaving the catheter in the vein and exposing the needle,
- depressing the second end of the tubular sheath to cause the jaws to slide out from the hole, resiliently open, and release the needle, permitting the needle to retract into the tubular sheath.

* * * * *